(12) United States Patent
Ebden et al.

(10) Patent No.: US 7,964,616 B2
(45) Date of Patent: Jun. 21, 2011

(54) COMPOUNDS 679

(75) Inventors: Mark Ebden, Leicestershire (GB);
Simon David Guile, Leicestershire (GB)

(73) Assignee: AstraZeneca AB, Sodertalje (SE)

( * ) Notice: Subject to any disclaimer, the term of this patent is extended or adjusted under 35 U.S.C. 154(b) by 585 days.

(21) Appl. No.: 12/052,908

(22) Filed: Mar. 21, 2008

(65) Prior Publication Data

US 2008/0234319 A1    Sep. 25, 2008

Related U.S. Application Data

(60) Provisional application No. 60/896,298, filed on Mar. 22, 2007.

(51) Int. Cl.
*A61K 31/04* (2006.01)
*C07D 215/38* (2006.01)

(52) U.S. Cl. ......... 514/313; 514/314; 546/159; 546/167
(58) Field of Classification Search ............... 546/159, 546/180, 167; 514/313, 314
See application file for complete search history.

(56) References Cited

U.S. PATENT DOCUMENTS

| | | | |
|---|---|---|---|
| 3,464,998 | A | 9/1969 | Krimmel |
| 3,471,491 | A | 10/1969 | Venkatachala et al. |
| 4,751,292 | A | 6/1988 | Fox |
| 5,643,925 | A | 7/1997 | Naruto et al. |
| 5,804,588 | A | 9/1998 | Dyke et al. |
| 6,949,539 | B2 | 9/2005 | Alcaraz et al. |
| 7,129,246 | B2 | 10/2006 | Alcaraz et al. |
| 7,408,065 | B2 | 8/2008 | Evans et al. |
| 2001/0003121 | A1 | 6/2001 | Baxter et al. |
| 2004/0236109 | A1 | 11/2004 | Van Straten et al. |
| 2008/0058293 | A1 | 3/2008 | Ford et al. |
| 2008/0058309 | A1 | 3/2008 | Cheshire et al. |
| 2008/0234319 | A1 | 9/2008 | Guile et al. |
| 2009/0143354 | A1 | 6/2009 | Evans et al. |
| 2009/0143428 | A1 | 6/2009 | Guile et al. |

FOREIGN PATENT DOCUMENTS

| | | |
|---|---|---|
| BE | 650919 | 7/1964 |
| DE | 1943404 | 12/1970 |
| EP | 0002065 | 5/1979 |
| EP | 0501656 | 9/1992 |
| EP | 0867436 | 9/1998 |
| EP | 0940391 | 9/1999 |
| WO | WO95/04720 | 2/1995 |
| WO | WO97/19926 | 6/1997 |
| WO | WO99/26927 | 6/1999 |
| WO | WO99/29660 | 6/1999 |
| WO | WO99/29661 | 6/1999 |
| WO | WO00/61569 | 10/2000 |
| WO | WO00/73283 | 12/2000 |
| WO | WO01/37826 | 5/2001 |
| WO | WO01/94338 | 12/2001 |
| WO | WO03/042190 | 5/2003 |
| WO | WO03/045313 | 6/2003 |
| WO | WO03/080579 | 10/2003 |
| WO | WO03/087037 | 10/2003 |
| WO | 2004106305 | * 12/2004 |
| WO | 2005009968 | * 2/2005 |
| WO | 2006059945 | * 6/2006 |

OTHER PUBLICATIONS

Korodi, CA125:275756, abstract only of Het Comm, vol. 2(3), pp. 219-226, 1996.*
Hirashima, CA114:201707, abstract only of Nippon Noyaku Gakkaishi, vol. 15(4), pp. 539-551, 1990.*
Biggs, J Med Chem, vol. 15(6), pp. 642-646, 1972.*
Hirashima, CA 118:56667, abstract only of Com Biochem and Phy, Part C, vol. 103C (2), pp. 321-325, 1992.*
Accession No. 2003:42109, CAS Registry No. 487064-48-2, 2003.
Agosta et al., "Preparation of 3-Hydroxycyclohexaneacetonitriles", *J. Org. Chem.* 46:4880-4885 (1981).
Alcaraz et al., Preparation of Adamantane Derivatives as P2X7 Receptor Antagonists, CAS Accession No. 2001:904155, 2001.
Alcaraz et al., "Novel P2X7 Receptor Antagonists" *Bioorganic and Medicinal Chemistry Letters*, 13:4043-4046 (2003).
Author unknown, online article from www.pharmaprojects.com/therapy_analysis/purin_P2X7_0109.htm, Jan. 2009.
Baxter et al., "Hit-to-Lead Studies: The Discovery of Potent Adamantane Amide P2X7 Receptor Antagonists," *Bioorganic and Medicinal Chemistry Letters*, 13:4047-4050 (2003).
Bourrie et al., "SSR125329A, A High Affinity Receptor Ligand with Potent Anti-Inflammatory Properties," *Eur. J. of Pharm.*, 456:123-131 (2002).
Costakis et al., "Synthesis of Some Adamantane Derivatives of 2-Aminobenzothiazoles", *Journal of Medicinal Chemistry* 14(12):1222-1223 (1971).
Ferrari et al., "Extracellular ATP Triggers IL-1β Release by Activating the Purinergic P2Z Receptor of Human Macrophages", *J. Imtnunol.* 159:1451-1458 (1997).

(Continued)

*Primary Examiner* — D. Margaret Seaman
(74) *Attorney, Agent, or Firm* — Fish & Richardson P.C.

(57) ABSTRACT

The invention provides compounds of formula (I), processes for their preparation, pharmaceutical compositions containing them, a process for preparing the pharmaceutical compositions, and their use in therapy, wherein $R^1$, $R^2$, $R^3$ and n are as defined in the specification

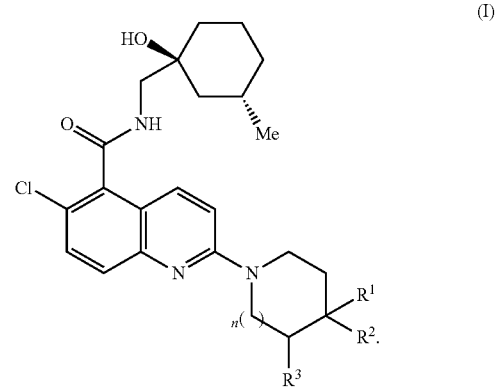

(I)

15 Claims, No Drawings

OTHER PUBLICATIONS

Ferrari et al., "Purinergic Modulation of Interleukin-1β Release from Microglial Cells Stimulated with Bacterial Endotoxin", *J. Exp. Med.* 185(3):579-582 (1997).

Fulop et al., "A Versatile Method for the Synthesis of *cis*-2-aminomethylcyclanols"*Synthetic Communications* 28(12):2303-2309 (1998).

Henderson et al., "Inhibition of interleukin-1-induced synovitis and articular cartilage proteoglycan loss in the rabbit knee by recombinant human interleukin-1 receptor antagonist", *Cytokine* 3(3):246-249 (1991).

Ho et al., "Synthesis of a Peptidomimetic Tricyclic Tetrahydrobenzo[*ij*] quinoline as a VLA-4 Antagonist", *J. Org. Chem.* 65:6743-6748, p. 6745, scheme 5, (27) (2000).

Kadota et al., "Significance of IL-1β and IL-1 receptor antagonist (IL-1Ra) in bronchoalveolar lavage fluid (BALF) in patients with diffuse panbronchiolitis (DPB)", *Clin Exp. Immunol.* 103:461-466 (1996).

Khurana et al., "Clinical aspects of rheumatoid arthritis", Pathophysiology, vol. 12, Issue 3, Abstract (2005).

Kirkham, "Interleukin-1, Immune Activation Pathways, and Different Mechanisms in Osteoarthritis and Rheumatoid Arthritis", *Annals of the Rheumatic Diseases*, 50:395-400 (1991).

Leonard et al., "Small Charged Rings. II. The Synthesis of Aziridinium Salts", *J. Am. Chem. Soc.* 84:4806-4813 (1962).

Li et al., "Should atherosclerosis be considered a cancer of the vascular wall?" *Medical Hypotheses*, 64:694-698 (2005).

Mackenzie et al., "Could rheumatoid arthritis have an infectious aetiology?" Drug Discovery Today: Disease Mechanism, vol. 2, Issue 3, Abstract (2005).

Miginiac et al., "Activation of Zinc by Trimethylchlorosilane: An Improved Procedure for the Preparation ofβ-Hydroxy Esters from Ethyl Bromoacetate and Aldehydes or Ketones (Reformatsky Reaction)", *J. Org. Chem.* 52:4796-4798 (1987).

Modena et al., "Plant Growth Regulating Activities of 2-[2-(Arylamino)-2-oxoethyl]benzoic acids", *Il Farmaco* 48(4):567-572 (1993).

Otterness et al., "Possible Role of IL-I in Arthritis: Effects of Prostaglandins in the Regulation of IL-1 Synthesis and Actions", Agent Act 39 (Suppl):109-120 (1993).

Richards et al., "Substituted 2-Phenyl-benzimidazole Derivatives: Novel Compounds that Suppress Key Markers of Allergy," Eur. J. of Medic. Chem., 41:950-969 (2006).

Sakito et al., "Interleukin 1β, Tumor Necrosis Factor Alpha, and Interleukin 8 in Bronchoalveolar Lavage Fluid of Patients with Diffuse Panbronchiolitis: A Potential Mechanism of Macrolide Therapy", *Respiration* 63:42-48 (1996).

Sharma et al., "Studies on Fusedβ-Lactams: Synthesis & Antibacterial Activity of Some Pyridyl/Quinolyl-2-azetidinones", *Indian Journal of Chemistry* 27B:494-497 (1988).

STN International, File REGISTRY, see RN 405068-97-5, 405070-41-9, 405076-22-4, Apr. 14, 2002.

STN International, File REGISTRY, see RN 445032-09-7, Aug. 30, 2002.

STN International, File CHEMCATS, Accession No. 2001:48444, May 14, 2001, NS18552, 2-Quinolinecarboxamide, N-(tricycle[3.3.1.13,7]dec-1-ylmethyl), CAS Registry No. 313688-07-2.

STN International, file CHEMCATS, Accession No. 2002:1977776, Jul. 9, 2002, BAS 1098675, "Cyclopropanecarboxamide, N-(2-methyl-5-quinolinyl)-", CAS Registry No. 333432-34-1.

STN International, file CHEMCATS, Accession No. Jan. 11, 2001, Cyclopropanecarboxamide, N-(2,6-dimethyl-5-quinolinyl)-(9CI)(CA INDEX NAME), CAS Registry No. 313479-89-9.

STN International, File REGISTRY, see RN 401622-10-4, Mar. 24, 2002.

STN International, File REGISTRY, Registry Copyright Jul. 14, 2006 ACS on STN RN: 892733-99-2,1 page.

STN International, File REGISTRY, Registry Copyright Aug. 8, 2006 ACS on STN RN: 899526-58-0, 1 page.

van den Berg, Lessons from animal models of osteoarthritis, *Curr. Opin. Rheumatol*, 13(5): 452-6 (2001).

Whitehead et al., "Diuretics. IV. 6-Chloro-3-substituted 7-Sulfamoyl-1,2,4-benzothiadiazine 1,1-Dioxides", *J. Org. Chem.* 26:2809-2813 (1961).

Yu et al., "Inhibition of IL-1 Release from Human Monocytes and Suppression of Streptococcal Cell Wall and Adjuvant-induced Arthritis in Rats by an Extract of *Tripterygium wilfordii* Hook", *Gen. Pharmac.* 25(6):1115-1122 (1994).

\* cited by examiner

COMPOUNDS 679

CROSS-REFERENCE TO RELATED APPLICATIONS

This application claims the benefit under 35 U.S.C. §119 (e) of U.S. Provisional Application No. 60/896,298, filed on Mar. 22, 2007, the contents of which is incorporated herein by reference in its entirety.

The present invention relates to quinoline derivatives, processes for their preparation, pharmaceutical compositions containing them, a process for preparing pharmaceutical compositions, and their use in therapy.

The $P2X_7$ receptor (previously known as P2Z receptor), which is a ligand-gated ion channel, is present on a variety of cell types, largely those known to be involved in the inflammatory/immune process, specifically, macrophages, mast cells and lymphocytes (T and B). Activation of the $P2X_7$ receptor by extracellular nucleotides, in particular adenosine triphosphate, leads to the release of interleukin-1β (IL-1β) and giant cell formation (macrophages/microglial cells), degranulation (mast cells) and proliferation (T cells) and apoptosis and L-selectin shedding (lymphocytes). $P2X_7$ receptors are also located on antigen-presenting cells (APC), keratinocytes, salivary acinar cells (parotid cells), hepatocytes and mesangial cells. It would be desirable to make compounds effective as $P2X_7$ receptor antagonists for use in the treatment of inflammatory, immune or cardiovascular diseases, in the aetiologies of which the $P2X_7$ receptor may play a role.

An important property for a drug acting as a $P2X_7$ receptor antagonist is that it has high potency. Moreover, it is also desirable for such drugs to possess good selectivity and pharmacokinetic properties in order to further enhance drug efficacy. As an example, it can be advantageous for such drugs to exhibit low activity against the human ether-a-go-go-related gene (hERG)-encoded potassium channel. In this regard, low activity against hERG binding in vitro is indicative of low activity in vivo.

$P2X_7$ antagonists comprising quinolinyl groups are known from WO2003/080579, WO 2004/106305, WO2005/009968 and WO2006/059945. It has now surprisingly been found that a narrow class of compounds generically disclosed in WO 2004/106305 exhibit advantageous pharmaceutical properties. For example, in addition to having high potency the compounds of the present invention exhibit very low activity against hERG binding, enhancing their suitability for use as pharmaceuticals.

In accordance with the present invention, there is therefore provided a compound of formula (I), or a pharmaceutically acceptable salt thereof,

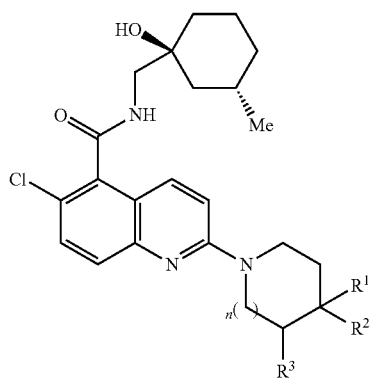

(I)

wherein n is 0 or 1;

when n is 0, $R^1$ represents hydrogen or methyl, $R^2$ represents hydroxyl and $R^3$ represents hydrogen; and when n is 1, $R^1$ represents hydrogen and one of $R^2$ and $R^3$ represents hydroxyl and the other of $R^2$ and $R^3$ represents hydrogen.

It will be understood that certain compounds of the present invention may exist in solvated, for example hydrated, as well as unsolvated forms. It is to be understood that the present invention encompasses all such solvated forms.

Compounds of the present invention show very high $P2X_7$ antagonist activity. In addition they have particularly low affinity for the human ether-a-go-go-related gene (hERG)-encoded potassium channel and therefore are advantageous with regard to safety margins.

Pharmaceutically acceptable salts of a compound of formula (I) include, but are not limited to acid addition salts such as a hydrochloride, hydrobromide, phosphate, acetate, fumarate, maleate, tartrate, citrate, oxalate, methanesulphonate or p-toluenesulphonate salt. In an embodiment of the invention pharmaceutically acceptable salts of a compound of formula (I) are selected from hydrochloride, hydrobromide, phosphate, tartrate, citrate, oxalate, methanesulphonate or p-toluenesulphonate salt.

The compounds of the present invention contain two chiral centres located on the cyclohexyl ring within formula (I). One of the chiral centers is located at the cyclohexyl ring atom to which the hydroxyl substituent is directly attached (the 1 position), and the other is located at the cyclohexyl ring atom to which the methyl substituent is directly attached (the 3 position). In the present invention, the stereochemical configuration at both these chiral centres is S ((1S,3S) stereoisomers), as designated by the Cahn-Ingold-Prelog system and as depicted in the structure of formula (I) below.

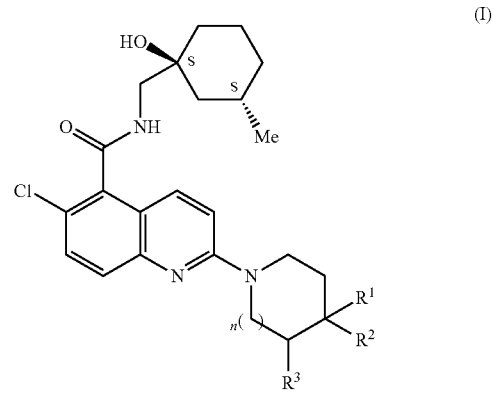

(I)

In embodiments of the invention wherein n is 0, the compounds of formula (I) contain a further chiral centre at the carbon atom to which both $R^1$ and $R^2$ are directly attached. The present invention encompasses compounds of all stereochemical configurations at this position, including mixtures thereof.

In an embodiment of the invention n is 0, $R^1$ represents hydrogen or methyl, $R^2$ represents hydroxyl and $R^3$ represents hydrogen.

In an embodiment of the invention, n is 0, $R^1$ represents hydrogen, $R^2$ represents hydroxyl and $R^3$ represents hydrogen. In one aspect of this embodiment, the chiral centre at the carbon atom to which $R^1$ and $R^2$ are directly attached has an S configuration. In another aspect of this embodiment, the chiral centre at the carbon atom to which $R^1$ and $R^2$ are directly attached has an R configuration.

In an embodiment of the invention, n is 0, $R^1$ represents methyl, $R^2$ represents hydroxyl and $R^3$ represents hydrogen.

In one aspect of this embodiment, the chiral centre at the carbon atom to which $R^1$ and $R^2$ are directly attached has an S configuration. In another aspect of this embodiment, the chiral centre at the carbon atom to which $R^1$ and $R^2$ are directly attached has an R configuration.

In an embodiment of the invention, n is 1, $R^1$ represents hydrogen and one of $R^2$ and $R^3$ represents hydroxyl and the other of $R^2$ and $R^3$ represents hydrogen.

In an embodiment of the invention, n is 1, $R^1$ represents hydrogen, $R^2$ represents hydroxyl and $R^3$ represents hydrogen.

In an embodiment of the invention, n is 1, $R^1$ represents hydrogen, $R^2$ represents hydrogen and $R^3$ represents hydroxyl. Compounds according to this embodiment contain a further chiral centre at the carbon atom to which $R^3$ is directly attached. The present invention encompasses all stereochemical configurations at this position, including mixtures thereof. In one aspect of this embodiment, the chiral centre at the carbon atom to which $R^3$ is directly attached has an S configuration. In another aspect of this embodiment, the chiral centre at the carbon atom to which $R^3$ is directly attached has an R configuration.

The compounds of the present invention contain two chiral centres located on the cyclohexyl ring within formula (I). The stereochemical configuration at both these chiral centres is S, i.e. they are (1S,3S) stereoisomers. For the avoidance of doubt, the (1S,3S) stereoisomers of the present invention may be present as a mixture with one or more of the other possible stereoisomers at these chiral centers, i.e. the (1R,3R), (1R,3S) and (1S,3R) stereoisomers. For example, the (1S,3S) stereoisomer may be present in a 1:1 mixture with the (1R,3R) stereoisomer.

In one embodiment, the present invention provides a compound of formula (I) which is optically pure at the (1S,3S) chiral centers. In a further embodiment, the present invention provides a compound of formula (I), which is optically pure at all its chiral centres.

In the context of the present specification, the term optically pure is defined in terms of enantiomeric excess (e.e.), and diastereomeric excess (d.e.), which are calculated from the ratio of the difference between the amounts of the respective enantiomers/diastereoisomers present and the sum of these amounts, expressed as a percentage. To illustrate, a preparation containing 95% of one enantiomer and 5% of another enantiomer has an enantiomeric excess (e.e.) of 90% [i.e. (95−5)/(95+5)×100]. Diastereomeric excess is defined by analogy to enantiomeric excess. Optically pure compounds according to the present invention have an e.e. of at least 90%. In an embodiment of the invention, optically pure compounds have an e.e. of at least 95%. In a further embodiment of the invention, optically pure compounds have an e.e. of at least 98%. Where the compound has diastereoisomers, optically pure compounds have an e.e. of at least 90% and a diastereomeric excess (d.e.) of at least 90%. In an embodiment of the invention, optically pure compounds have an e.e. of at least 95% and a d.e. of at least 95%. In a further embodiment of the invention, optically pure compounds have an e.e. of at least 98% and a d.e. of at least 98%.

In an embodiment of the invention, the compound of formula (I) is selected from:

6-chloro-N-{[(1S,3S)-1-hydroxy-3-methylcyclohexyl]methyl}-2-[(3S)-3-hydroxypyrrolidin-1-yl]quinoline-5-carboxamide, 6-chloro-N-{[(1S,3S)-1-hydroxy-3-methylcyclohexyl]methyl}-2-[(3R)-3-hydroxypyrrolidin-1-yl]quinoline-5-carboxamide, 6-chloro-N-{[(1S,3S)-1-hydroxy-3-methylcyclohexyl]methyl}-2-(4-hydroxypiperidin-1-yl)quinoline-5-carboxamide, and 6-chloro-N-{[(1S,3S)-1-hydroxy-3-methylcyclohexyl]methyl}-2-(3-hydroxy-3-methylpyrrolidin-1-yl)quinoline-5-carboxamide or a pharmaceutically acceptable salt thereof.

The present invention further provides a process for the preparation of a compound of formula (I) as defined above, or a pharmaceutically acceptable salt thereof, which comprises:
(a) reacting a compound of formula

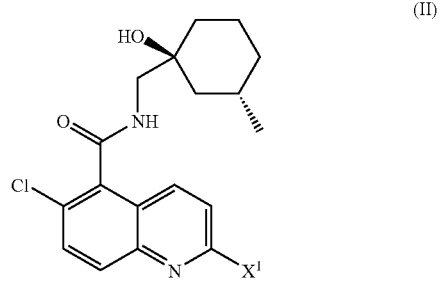

(II)

wherein $X^1$ represents a suitable leaving group (e.g. halogen, paratoluene sulfonate, methane sulfonate or trifluoromethane sulfonate) with a compound of formula (III)

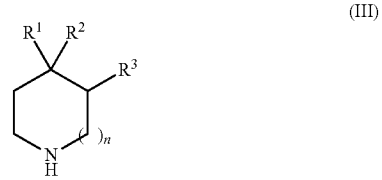

(III)

wherein $R^1$, $R^2$, $R^3$ and n are as defined in formula (I), and optionally forming a pharmaceutically acceptable salt of the compound.

The reaction of (II) and (III) may be performed in an organic solvent such as methanol, acetonitrile, N,N-dimethylformamide, dimethyl sulfoxide or 1-methyl-2-pyrrolidinone, and in the presence of a suitable base such as sodium hydride, triethylamine, diisopropylethylamine or potassium carbonate at a temperature in the range from 50° C. to 150° C., in particular from 80° C. to 120° C., either in a microwave or by conventional thermal conditions.

Compounds of formula (III) as either the free base or as a salt (acceptable salts of a compound of formula (III) include, but are not limited to acid addition salts such as a hydrochloride, hydrobromide, phosphate, acetate, fumarate, maleate, tartrate, citrate, oxalate, methanesulphonate or p-toluenesulphonate salt) are either commercially available, are known in the literature or may be prepared using known techniques by those skilled in the art.

Compounds of formula (II) may be prepared by reacting a compound of formula (IV)

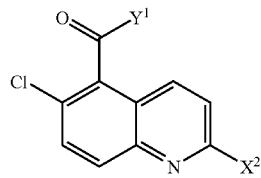
(IV)

wherein $X^2$ represents a leaving group (e.g. halogen, paratoluene sulfonate, methane sulfonate or trifluoromethane sulfonate) and $Y^1$ represents a suitable leaving group (e.g. hydroxyl or chloro) with (1S,3S)-1-(aminomethyl)-3-methylcyclohexanol (Compound (V)).

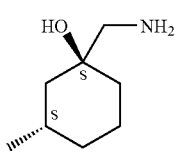
(V)

In the reaction of (IV) and (V) where $Y^1$ represents a chlorine radical the reaction may be conveniently carried out in an organic solvent such as acetone, dichloromethane, N,N-dimethylformamide or 1-methyl-2-pyrrolidinone with a suitable base such as potassium carbonate, diisopropylethylamine or triethylamine. Where $Y^1$ represents a hydroxyl group, it may be necessary or desirable to use a coupling agent such as bromo-tris-pyrrolidino-phosphonium hexafluorophosphate (PyBroP), 1-(3-dimethylaminopropyl)-3-ethylcarbodiimide (EDCI) or O-(benzotriazol-1-yl)-N,N,N',N'-tetramethyluronium tetrafluoroborate (TBTU). If $Y^1$ is a chlorine radical, such compounds may be conveniently prepared by treatment of the corresponding carboxylic acid derivative under standard conditions (such as thionyl chloride or oxalyl chloride in dichloromethane).

The compound of formula (V) is a novel compound and forms a further aspect of the present invention. Accordingly, a further aspect of the present invention provides a compound which is (1S,3S)-1-(aminomethyl)-3-methylcyclohexanol, or a salt thereof. In an embodiment of this aspect, the compound (1S,3S)-1-(aminomethyl)-3-methylcyclohexanol is optically pure (optically pure being as defined as for optically pure compounds of formula (I)). Salts of (1S,3S)-1-(aminomethyl)-3-methylcyclohexanol include acid addition salts such as a hydrochloride or hydrobromide.

(1S,3S)-1-(aminomethyl)-3-methylcyclohexanol (V) may be prepared by reacting a compound of formula (VI) with a suitable protected ammonia equivalent such as phthalimide (followed by treatment with hydrazine), di-tert-butyl imidodicarbonate (followed by treatment with an acid e.g. hydrogen chloride), benzylamines, for example, 4-methoxybenzylamine (followed by treatment with 2,3-dichloro-5,6-dicyano-1,4-benzoquinone (DDQ) or alternatively benzylamine, N-benzyl-1-methanamine or 1,1-diphenylmethanamine (followed by deprotection with hydrogen in the presence of a suitable metal catalyst).

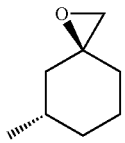
(VI)

The reaction between the compound of formula (VI) and a benzylamine may conveniently be carried out in protic solvents such as methanol or ethanol (optionally as mixed solvent systems with toluene) or aprotic solvents such as acetonitrile, tetrahydrofuran or N,N-dimethylformamide at a temperature in the range from 25° C. to 140° C., in particular at 65° C. to 100° C., either in a microwave or under conventional thermal conditions. Subsequent removal of the benzyl protecting group may conveniently be carried out under hydrogenolysis conditions in a protic solvent such as methanol, ethanol or acetic acid or aprotic solvents such as ethyl acetate at a temperature in the range from 25° C. to 100° C., preferably at 25° C., under a hydrogen atmosphere at 1 to 5 bar, preferably at 4 bar in the presence of a catalyst such as palladium on carbon, platinum oxide or rhodium on carbon, preferably palladium on carbon. The compound (VI) is known in the literature (Alexakis, A. et al., Synlett 2001, No. 9, 1375). A detailed example of a preparation of (1S,3S)-1-(aminomethyl)-3-methylcyclohexanol is given hereinafter in the examples.

Compounds of formula (IV) wherein $X^2$ represents a leaving group (e.g. halogen, paratoluene sulfonate, methane sulfonate or trifluoromethane sulfonate) and $Y^1$ represents hydroxyl may be prepared from a compound of formula (VII)

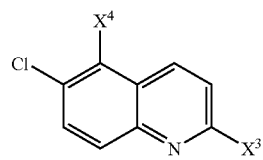
(VII)

wherein $X^3$ represents a leaving group (e.g. halogen, paratoluene sulfonate, methane sulfonate or trifluoromethane sulfonate) and $X^4$ represents an iodine or bromine radical.

In the conversion of (VII) to (IV) the reaction may be conveniently carried out by metal/halogen exchange followed by an electrophilic quench with carbon dioxide. The reaction may be performed in an organic solvent such as tetrahydrofuran, diethyl ether, diglyme or hexane with an organometallic reagent such as butyllithium, sec-butyllithium, tert-butyllithium or isopropylmagnesium chloride at a temperature in the range of −78° C. to 25° C., (e.g. 25° C. for the metal/halogen exchange and 0° C. for the reaction with carbon dioxide).

(VII) may also be converted to (IV) by reacting under carbonylation conditions in water as solvent at a temperature of 25° C. to 120° C., under an atmosphere of carbon monoxide of 1 to 8 bar in the presence of a metal catalyst (e.g. 1,1'-bis(diphenylphosphino)ferrocenedichloro palladium (II) or 1,1'-bis(di-tert-butylphosphino)ferrocenedichloro palladium (II) (Pd-118)) in the presence of an amine base (e.g. triethylamine or diisopropylethylamine).

Compounds of formula (II) wherein $X^1$ represents a suitable leaving group (e.g. halogen, paratoluene sulfonate, methane sulfonate or trifluoromethane sulfonate) may be prepared from compounds of formula (VII) wherein $X^3$ represents a leaving group (e.g. halogen, paratoluene sulfonate, methane sulfonate or trifluoromethane sulfonate) and $X^4$ represents an iodine or bromine radical.

In the conversion of (VII) to (II) the reaction may be conveniently carried out in an organic solvent such as N-methylpyrrollidine, N,N-dimethylformamide, N,N-dimethylacetamide, tetrahydrofuran or acetonitrile in the presence of amine (V) at a temperature of 25° C. to 120° C., under an atmosphere of carbon monoxide of 1 to 8 bar, in the presence of a metal catalyst (e.g. 1,1'-bis(diphenylphosphino)ferrocenedichloro palladium (II) or 1,1'-bis(di-tert-butylphosphino)ferrocenedichloro palladium (II) (Pd-118)) and in the presence of an amine base (e.g. triethylamine or diisopropylethylamine).

Compounds of formula (VII) wherein $X^3$ represents a leaving group (e.g. halogen, paratoluene sulfonate, methane sulfonate or trifluoromethane sulfonate) and $X^4$ represents an iodine or bromine radical may be prepared from a compound of formula (VIII)

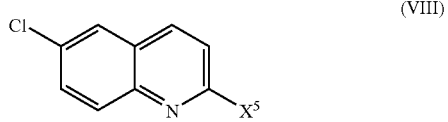

(VIII)

wherein $X^5$ represents a leaving group (e.g. halogen, paratoluene sulfonate, methane sulfonate or trifluoromethane sulfonate).

In the conversion of (VIII) to (VII) wherein $X^3$ represents an iodine radical the reaction may be conveniently carried out in an acid such as fuming sulfuric acid or triflic acid in the presence of an iodine source such as iodine ($I_2$), N-iodosuccinimide (NIS) or iodine monochloride (ICl) in the presence or absence of a metal salt (e.g. silver trifluoromethane sulfonate or silver sulfate).

Compounds of formula (VIII) are either commercially available, are known in the literature or may be prepared using known techniques by those skilled in the art. For example, the compound of formula (VIII) wherein $X^5$ is a chlorine radical is known in the literature (Inglis, S. R., et al., J. Med. Chem., 2004, 47, 5405).

The compound of formula (VII), wherein $X^3$ is a chlorine radical and $X^4$ is an iodine radical, is a novel compound and forms a further aspect of the present invention.

Accordingly, a further aspect of the present invention provides a compound which is 2,6-dichloro-5-iodoquinoline.

The compounds of formula (II) are novel compounds and form a further aspect of the present invention. One embodiment of the invention provides compounds of formula (II) wherein $X^1$ is selected from halogen, paratoluene sulfonate, methane sulfonate and trifluoromethane sulfonate.

Another embodiment of the invention provides a compound of formula (II) wherein $X^1$ is a chlorine radical. Accordingly, a further aspect of the present invention provides a compound which is 2,6-dichloro-N-{[(1S,3S)-1-hydroxy-3-methylcyclohexyl]methyl}quinoline-5-carboxamide.

It will be appreciated by those skilled in the art that in the processes of the present invention certain functional groups such as hydroxy, carboxyl or amino groups in the starting reagents or intermediate compounds may need to be protected by protecting groups. Thus, the preparation of the compounds of formula (I) may involve at a certain stage protection with and/or the removal of one or more protecting groups. The protection and deprotection of functional groups is described in 'Protective Groups in Organic Synthesis', 2nd edition, T. W. Greene and P. G. M. Wuts, Wiley-Interscience (1991) and 'Protecting Groups', P. J. Kocienski, Georg Thieme Verlag (1994). The compounds of formula (I) above may be converted to a pharmaceutically acceptable salt using conventional methods.

The compounds of the present invention have beneficial potency, selectivity and/or pharmacokinetic properties. For example, compounds of the present invention have low affinity for the human ether-a-go-go-related-gene (hERG)-encoded potassium channel. In this regard, drugs interacting with the hERG-encoded potassium channel and consequently restoration of the negative cell potential by $K^+$ efflux, can cause a prolongation of the QT interval, leading to an acquired long QT syndrome (LQT) [M. C. Sanguinetti, C Jiang, M. E. Curran, M. T. Keating, Cell 1995, 81, 299-307; and K. Finlayson et al., Eur. J. Pharm. 2004, 500, 129-142]. This, in consequence, may induce a potentially fatal arrythmia, known as torsade de points (TdP) [W. Haferkamp et al., Eur. Heart J. 2000, 21, 1216-1331]. New chemical entities, if not intended for cardiovascular use, which are lacking effects on cardiac channels, and the hERG channel in particular, will therefore provide an improved safety profile and so gain a therapeutic and regulatory advantage over drugs with QT prolonging effects. Kiss et al (Assay Drug Dev. Technol. 2003, 1, 127-135) describe a method of assaying compounds for their ability to inhibit ion channel activity such as hERG. Springthorpe and Strandlund (WO 2005037052) describe a method of assaying compounds for their ability to bind to the IKr potassium (hERG).

Compounds according to the present invention also display good bioavailability as determined by pharmacokinetic parameters. For example, compounds according to the present invention may display low plasma protein binding. The compound according to the present invention may also display low activity in an in vitro phospholipidosis screen.

A compound of the invention, or a pharmaceutically acceptable salt thereof, may be of benefit in the treatment of:
1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;
2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthritides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritus ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

Accordingly, the present invention provides a compound of formula (I), or a pharmaceutically acceptable salt thereof, as hereinbefore defined for use in therapy.

In another aspect, the invention provides the use of a compound of formula (I), or a pharmaceutically acceptable salt thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

In another aspect, the invention provides a compound of formula (I), or a pharmaceutically acceptable salt thereof, as hereinbefore defined for treating rheumatoid arthritis.

In another aspect, the invention provides a compound of formula (I), or a pharmaceutically acceptable salt thereof, as hereinbefore defined for treating inflammatory bowel disease.

In another aspect, the invention provides a compound of formula (I), or a pharmaceutically acceptable salt thereof, as hereinbefore defined for treating Crohn's disease.

In another aspect, the invention provides the use of a compound of formula (I), or a pharmaceutically acceptable salt thereof, as hereinbefore defined in the manufacture of a medicament for use in the treatment of rheumatoid arthritis.

In another aspect, the invention provides the use of a compound of formula (I), or a pharmaceutically acceptable salt thereof, as hereinbefore defined, in the manufacture of a medicament for use in the treatment of asthma or chronic obstructive pulmonary disease.

In another aspect, the invention provides the use of a compound of formula (I), or a pharmaceutically acceptable salt thereof, as hereinbefore defined in the manufacture of a medicament for use in the treatment of inflammatory bowel disease.

In another aspect, the invention provides the use of a compound of formula (I), or a pharmaceutically acceptable salt thereof, as hereinbefore defined in the manufacture of a medicament for use in the treatment of Crohn's disease.

The invention also provides a method of treating rheumatoid arthritis which comprises administering a therapeutically effective amount of a compound of formula (I), or a pharmaceutically acceptable salt thereof, as hereinbefore defined to a patient in need thereof.

The invention also provides a method of treating inflammatory bowel disease which comprises administering a therapeutically effective amount of a compound of formula (I), or a pharmaceutically acceptable salt thereof, as hereinbefore defined to a patient in need thereof.

The invention also provides a method of treating Crohn's disease which comprises administering a therapeutically effective amount of a compound of formula (I), or a pharmaceutically acceptable salt thereof, as hereinbefore defined to a patient in need thereof.

The invention also provides a method of treating an obstructive airways disease (e.g. asthma or COPD) which comprises administering a therapeutically effective amount of a compound of formula (I), or a pharmaceutically acceptable salt thereof, as hereinbefore defined to a patient in need thereof.

In order to use a compound of the invention, or a pharmaceutically acceptable salt thereof, for the therapeutic treatment of a warm-blooded animal, such as man, said ingredient is normally formulated in accordance with standard pharmaceutical practice as a pharmaceutical composition.

Therefore in another aspect the present invention provides a pharmaceutical composition which comprises a compound of the formula (I), or a pharmaceutically acceptable salt thereof (active ingredient), and a pharmaceutically acceptable adjuvant, diluent or carrier. In a further aspect the present invention provides a process for the preparation of said composition which comprises mixing active ingredient with a pharmaceutically acceptable adjuvant, diluent or carrier. Depending on the mode of administration, the pharmaceutical composition will, for example, comprise from 0.05 to 99% w (percent by weight), such as from 0.05 to 80% w, for example from 0.10 to 70% w, such as from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 0.1 mg and 1 g of active ingredient.

In another aspect a pharmaceutical composition of the invention is one suitable for intravenous, subcutaneous or intramuscular injection. Each patient may receive, for example, an intravenous, subcutaneous or intramuscular dose of 0.01 mgkg$^{-1}$ to 100 mgkg$^{-1}$ of the compound, for example in the range of 0.1 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine. Cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-I) interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline. In addition the invention relates to a combination of a compound of the invention with a monoclonal antibody targeting B-Lymphocytes (such as CD20 (rituximab), MRA-aIL16R and T-Lymphocytes, CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739, 010; a 2-cyanoquinoline compound such as L-746,530; or an indole or quinoline compound such as MK-591, MK-886, and BAY x 1005.

The present invention further relates to the combination of a compound of the invention, or a pharmaceutically acceptable salt thereof, and a receptor antagonist for leukotrienes (LT) B4, LTC4, LTD4, and LTE4 selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B1.- or B2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) capsaicin cream; (xviii) tachykinin NK1 or NK3 receptor antagonist such as NKP-608C, SB-233412 (talnetant) or D-4418; (xix) elastase inhibitor such as UT-77 or ZD-0892; (xx) induced nitric oxide synthase (iNOS) inhibitor; (xxi) chemoattractant receptor-homologous molecule expressed on TH2 cells, (such as a CRTH2 antagonist); (xxii) inhibitor of P38; (xxiii) agent modulating the function of Toll-like receptors (TLR), (xxiv) agent modulating the activity of another purinergic receptor; or (xxv) inhibitor of transcription factor activation such as NFkB, API, or STATS.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;
(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or
(ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The invention will now be further explained by reference to the following illustrative examples. In the examples the NMR spectra were measured on a Varian Unity spectrometer at a proton frequency of either 300 or 400 MHz. The MS spectra were measured on either an Agilent 1100 MSD G1946D spectrometer or a Hewlett Packard HP1100 MSD G1946A spectrometer. Preparative HPLC separations were performed using a Waters Symmetry® or Xterra® column using 0.1% aqueous trifluoroacetic acid: acetonitrile, 0.1% aqueous ammonia: acetonitrile or 0.1% ammonium acetate: acetonitrile as the eluant. Microwave reactions were performed in a CEM Discover single mode microwave. Compounds and intermediates were named by the IUPAC naming package provided by ACD Labs, Toronto, Canada.

EXAMPLE 1

6-Chloro-N-{[(1S,3S)-1-hydroxy-3-methylcyclohexyl]methyl}-2-[(3S)-3-hydroxypyrrolidin-1-yl]quinoline-5-carboxamide

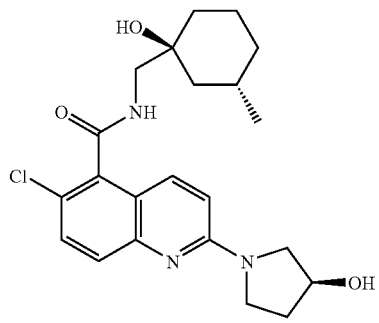

a) (3S,5S)-5-Methyl-1-oxaspiro[2.5]octane

The subtitle compound was prepared according to the literature procedure (Weijers, C. A. G. M. et al., JOC. 2005, 70, 6639-6646) by reacting a solution of potassium tert-butoxide (7.84 g) in dimethylsulfoxide (200 ml) with a mixture of (3S)-3-methylcyclohexanone (4.0 g, >98% ee) (Alexakis, A. et al., Synlett 2001, No. 9, 1375 and Hiemstra, H. and Wynberg, H., Tetrahedron Lett., 1977, 2183) and trimethylsulfoxonium iodide (15.4 g) in dimethylsulfoxide (100 ml) to afford the subtitle compound (3.5 g).
$^1$H NMR $\delta_{(CDCl_3)}$ 2.62 (2H, m), 1.86-1.56 (5H, m), 1.26 (2H, m), 0.99 (1H, m), 0.92 (3H, d), 0.86 (1H, m).

b) (1S,3S)-1-[(Benzylamino)methyl]-3-methylcyclohexanol

A methanol (1 ml) solution of benzylamine (5.9 g) and (3S,5S)-5-methyl-1-oxaspiro[2.5]octane (3.5 g) were heated in a microwave (100 W) for 30 minutes at 100° C., then concentrated in vacuo and purified by flash column chromatography (SiO$_2$, 20% ethyl acetate/iso-hexane as eluent) to afford the subtitle compound as a colourless oil (4.5 g).
m/z 234 (M+H, 100%).

c) (1S,3S)-1-(Aminomethyl)-3-methylcyclohexanol.HCl

A mixture of (1S,3S)-1-[(benzylamino)methyl]-3-methylcyclohexanol (4.5 g) and 5% palladium on carbon (500 mg) in methanol (40 ml) was stirred under a hydrogen atmosphere of 4 bar for 72 hours. The reaction was filtered through celite, washed with methanol (2×) and concentrated in vacuo to afford 1S,3S)-1-(Aminomethyl)-3-methylcyclohexanol as a colourless oil (2.5 g).
$^1$H NMR $\delta_{(CDCl_3)}$ 2.53 (2H, d), 1.50-1.90 (6H, cm), 1.06 (2H, m), 0.87 (3H, d) and 0.81 (2H, m).
(1S,3S)-1-(Aminomethyl)-3-methylcyclohexanol was readily converted to the subtitle compound by treatment as a solution in diethyl ether with 1 molar equivalent of 4M HCl in 1,4-dioxane.

d) 2,6-Dichloro-N-{[(1S,3S)-1-hydroxy-3-methylcyclohexyl]methyl}quinoline-5-carboxamide To a stirred suspension of 2,6-dichloro-quinoline-5-carboxylic acid (2.40 g) (WO2004/106305, Example 76, step b) in dichloromethane (100 ml) was added oxalyl chloride (3.15 g, 2.16 ml) and a drop of N,N-dimethylformamide. The reaction was stirred at room temperature for 2 hours before the volatiles were removed in vacuo and the residue diluted in dichloromethane (100 ml). To this solution were added (1S,3S)-1-(aminomethyl)-3-methylcyclohexanol.HCl (1.78 g) and diisopropylethylamine (6.70 ml) and the reaction stirred for 20 hours before washing with water. The organic layer was dried (MgSO$_4$), filtered and the volatiles were evaporated to provide a crude solid. The material was recrystallised from toluene to provide the subtitle compound as a beige solid (2.5 g).
$^1$H NMR $\delta_{(CDCl_3)}$ 8.24 (1H, d), 7.99 (1H, d), 7.71 (1H, t), 7.46 (1H, d), 6.34 (1H, s), 3.56 (2H, d), 1.82-1.52 (7H, m), 1.35 (1H, td), 1.07 (1H, t), 0.93 (3H, d), 0.88 (1H, dd).

e) 6-Chloro-N-{[(1S,3S)-1-hydroxy-3-methylcyclohexyl]methyl}-2-[(3S)-3-hydroxy-pyrrolidin-1-yl]quinoline-5-carboxamide (S)-3-hydroxypyrrolidine (80 mg) was added to a suspension of the product of step d) (0.2 g) and diisopropylethylamine (300 μl) in acetonitrile (3 ml). The reaction mixture was heated in a microwave (100 W) for 30 minutes at 120° C. before being concentrated in vacuo. Water (15 ml) was added and the suspension sonicated for 10 minutes. The solid was filtered and dried in vacuo overnight to afford the title compound as a cream solid (180 mg). m.p. 222° C. (acetonitrile).
m/z 418 (M+H, 100%), 416 (M−H, 100%)

$^1$H NMR $\delta_{(DMSO)}$ 8.49 (1H, t), 7.81 (1H, d), 7.54 (1H, d), 7.49 (1H, d), 6.95 (1H, d), 4.99 (1H, d), 4.42 (1H, s), 4.15 (1H, s), 3.59 (3H, m), 3.47 (1H, s), 3.28 (2H, d), 2.04 (1H, m), 1.92 (1H, m), 1.73 (1H, m), 1.64-1.41 (5H, m), 1.29 (1H, m), 1.04 (1H, t), 0.84 (3H, d), 0.75 (1H, m).

EXAMPLE 2

6-Chloro-N-{[(1S,3S)-1-hydroxy-3-methylcyclohexyl]methyl}-2-[(3R)-3-hydroxypyrrolidin-1-yl]quinoline-5-carboxamide

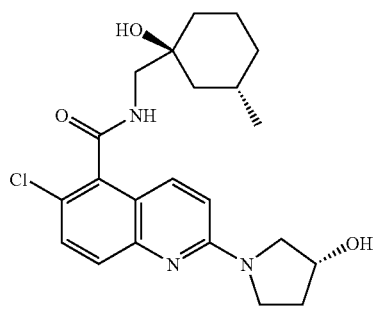

The title compound was prepared by the method of Example 1, step e) by reacting (R)-3-hydroxypyrrolidine (80 mg) (instead of (S)-3-hydroxypyrrolidine) with the product of Example 1, step d) (0.2 g) and diisopropylethylamine (300 μl) in acetonitrile (3 ml) to afford the title compound as a cream solid (190 mg). m.p. 222-223° C. (acetonitrile).

m/z 418 (M+H, 100%).

$^1$H NMR $\delta_{(CD_3OD)}$ 7.92 (1H, d), 7.65 (1H, d), 7.49 (1H, d), 6.94 (1H, d), 4.54 (1H, d), 3.69 (3H, m), 3.62 (1H, m), 3.41 (2H, s), 2.15 (1H, m), 2.10 (1H, m), 1.86-1.53 (6H, br. m), 1.40 (1H, m), 1.12 (1H, t), 0.89 (3H, d), 0.85 (1H, q).

EXAMPLE 3

6-Chloro-N-{[(1S,3S)-1-hydroxy-3-methylcyclohexyl]methyl}-2-(4-hydroxypiperidin-1-yl)quinoline-5-carboxamide

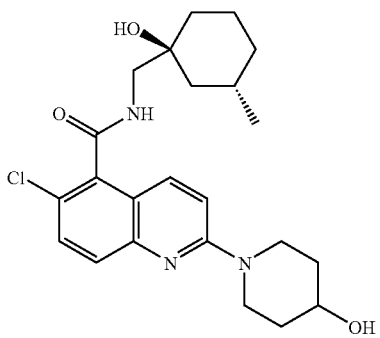

The title compound was prepared by the method of Example 1, step e) by reacting piperidin-4-ol (28 mg) (instead of (S)-3-hydroxypyrrolidine) with the product of Example 1, step d) (0.10 g) and diisopropylethylamine (0.11 g) in acetonitrile (2 ml) to afford the title compound as a white solid (99 mg). m.p. 120° C. dec.

m/z 432 (M+H, 100%), 430 (M−H, 100%)

$^1$H NMR $\delta_{(DMSO)}$ 8.46 (1H, t), 7.79 (1H, d), 7.52 (1H, d), 7.49 (1H, d), 7.32 (1H, d), 4.71 (1H, d), 4.18 (2H, m), 4.13 (1H, s), 3.73 (1H, m), 3.37-3.20 (4H, m), 1.84-1.21 (11H, m), 1.02 (1H, t), 0.82 (3H, d), 0.73 (1H, m)

EXAMPLE 4

6-Chloro-N-{[(1S,3S)-1-hydroxy-3-methylcyclohexyl]methyl}-2-(3-hydroxy-3-methylpyrrolidin-1-yl)quinoline-5-carboxamide

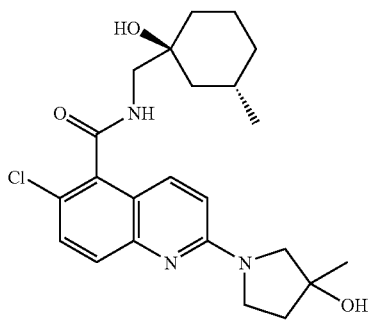

a) 1-Benzyl-3-methylpyrrolidin-3-ol

Methylmagnesium bromide (4 ml of 3M solution in diethyl ether) was added dropwise to a solution of 1-benzylpyrrolidin-3-one (1.75 g) in tetrahydrofuran (50 ml) at 0° C. The mixture was stirred at 0° C. for 1 hour before water and diethyl ether were added and the layers separated. The organic layer was washed with brine, dried (MgSO$_4$), filtered and concentrated in vacuo. The crude material was purified by flash column chromatography (SiO$_2$, 5% methanol/dichloromethane as eluent) to afford the subtitle compound as a pale brown oil (0.8 g).

$^1$H NMR $\delta_{(CDCl_3)}$ 7.34-7.20 (5H, m), 3.63 (2H, s), 3.00-2.92 (1H, m), 2.71 (1H, d), 2.37-2.28 (1H, m), 2.22 (1H, d), 1.92-1.84 (2H, m), 1.33 (3H, s).

b) 3-Methylpyrrolidin-3-ol

A slurry of 5% palladium on carbon in ethanol (1 ml) was added to a solution of 1-benzyl-3-methylpyrrolidin-3-ol (0.8 g) in methanol (10 ml) and the reaction stirred under a hydrogen atmosphere at 5 bar pressure for 4 days before filtering through celite and washing with ethanol (100 ml). The volatiles were removed in vacuo to provide the subtitle product as a yellow oil (0.42 g).

$^1$H NMR $\delta_{(CDCl_3)}$ 3.18 (1H, m), 2.96 (1H, m), 2.90 (1H, d), 2.68 (1H, d), 1.82 (2H, m), 1.41 (3H, s).

c) 6-Chloro-N-{[(1S,3S)-1-hydroxy-3-methylcyclohexyl]methyl}-2-(3-hydroxy-3-methylpyrrolidin-1-yl)quinoline-5-carboxamide The title compound was prepared by the method of Example 1, step e) by reacting 3-methylpyrrolidin-3-ol (0.42 g) (instead of (S)-3-hydroxypyrrolidine) with 2,6-dichloroquinoline-5-carboxylic acid (1-hydroxy-3-methyl-cyclohexylmethyl)-amide (0.10 g) and triethylamine (0.38 ml) (instead of diisopropylethylamine) in acetonitrile (1 ml) to afford the title compound crude and as a 1:1 mixture of diastereomers. The reaction was concentrated in vacuo and the products isolated by flash column chromatography (SiO$_2$, 4% methanol/dichloromethane as eluent) as a colourless solid (70 mg). The diastereomers were separated by supercritical fluid chromatography (SFC) on an OJ Daicel column using 25% ethanol/carbon dioxide as eluent to afford Isomer 1 as a colourless solid (18 mg).

m.p. 195-200° C. dec.

m/z 432 (M+H, 100%), $^1$H NMR $\delta_{(DMSO)}$ 8.48 (1H, t), 7.80 (1H, d), 7.55-7.46 (2H, m), 6.92 (1H, d), 4.82 (1H, s), 4.14 (1H, s), 3.70-3.49 (2H, m), 3.38 (1H, d), 3.27 (1H, d), 2.54-2.46 (2H, m), 1.99-1.42 (8H, m), 1.37 (3H, s), 1.34-1.22 (1H, m), 1.04 (1H, t), 0.84 (3H, d), 0.81-0.68 (1H, m), and Isomer 2 as a colourless solid (17 mg), m.p. 200-202° C., m/z 432 (M+H, 100%), $^1$H NMR $\delta_{(DMSO)}$ 8.48 (1H, t), 7.80 (1H, d), 7.54-7.48 (2H, m), 6.83 (1H, d), 4.82 (1H, s), 4.14 (1H, s), 3.70-3.48 (2H, m), 3.38 (1H, d), 3.28 (1H, d), 2.53-2.48 (2H, m), 2.02-1.42 (8H, m), 1.37 (3H, s), 1.33-1.21 (1H, m), 1.04 (1H, t), 0.84 (3H, d), 0.80-0.68 (1H, m).

EXAMPLE 5

6-Chloro-N-{[(1S,3S)-1-hydroxy-3-methylcyclohexyl]methyl}-2-[(3R)-3-hydroxypyrrolidin-1-yl]quinoline-5-carboxamide (Alternative Preparation to Example 2)

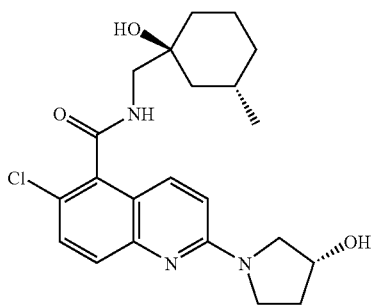

General conditions for Example 5: NMR spectra were measured on a Bruker Avance 360 MHz, Bruker Avance 400 MHz or Bruker DPX250 250 MHz spectrometer. Analytical stereochemical HPLC determinations were performed using ACE 3 Phenyl, 150×3 mm and a Chirapak AD-H 150×4.6 mm columns using 0.1% aqueous ammonium acetate: acetonitrile gradient elution and 19.9:80:0.1 isopropanol:isohexane:triethylamine isocratic elution respectively a) 2,6-Dichloroquinoline Phosphorus oxychloride (16.72 Kg) was charged to a vessel containing 6-chloroquinolin-2(1H)-one (12.50 Kg) (Prepared according to method of Johnston K. M. et al., J. Chem. Soc. Perkin Trans. 1, 1972, 1648 and references therein), benzyltrimethylammonium chloride (1.575 Kg) and 1,2-dimethoxyethane (87.8 Kg) at 70° C. 1,2-dimethoxyethane (22.5 Kg) was charged as a line rinse. The reaction was stirred at 70° C. to 75° C. for ca. 6 hours before the batch was concentrated to ca. 44 L by vacuum distillation (<40° C.). The concentrate was diluted with dichloromethane (253.1 Kg), adjusted to 38° C. to 45° C. and quenched by the addition of water (37.5 Kg) whilst maintaining the temperature at 38° C. to 45° C. After 70 minutes the batch was cooled to 25° C. to 30° C. and treated with Celite (1.30 Kg) for 40 minutes. The slurry was pressure filtered via a 1 μm filter membrane and the filtrates diluted with dichloromethane (87.5 Kg). The phases were separated and the aqueous phase extracted twice with dichloromethane (82 Kg). The combined organic extracts were washed sequentially with 5% w/w sodium hydrogen carbonate solution (37 L), water (37 Kg) and then concentrated to ca. 75 L at 25° C. to 40° C. Isopropanol (96.5 Kg) was charged and the batch then concentrated to ca. 75 L at 25° C. to 40° C. Isopropanol (95.4 Kg) was charged and the batch then concentrated to ca. 75 L at 25° C. to 40° C. The resultant slurry was stirred at 16° C. to 18° C. for 2 hours and then filtered. The filter cake was washed with isopropanol (19.7 Kg) at ca. 20° C. and then dried at up to 50° C. in vacuo to provide the subtitle compound as an off white solid (12.04 Kg).

$^1$H NMR $\delta_{(DMSO)}$ 8.45 (1H, d), 8.22 (1H, d), 7.99 (1H, d), 7.86 (1H, dd), 7.68 (1H, d).

b) 2,6-Dichloro-5-iodoquinoline 2,6-Dichloroquinoline (12.04 Kg) was charged to trifluoromethanesulphonic acid (80.6 Kg) in ten approximately equal portions such that the temperature was maintained at 15° C. to 25° C. N-iodosuccinimide (13.74 Kg) was then charged in five approximately equal portions such that the temperature was maintained at 15° C. to 25° C. The reaction was stirred at 20° C. to 25° C. for ca. 36 hours. The temperature was adjusted to 15° C. to 20° C., diluted with dichloromethane (159.4 Kg), adjusted to 5° C. to 10° C. and quenched by the addition of water (96.5 Kg) whilst maintaining the temperature at 5° C. to 23° C. The slurry was clarified via a 1 μm filter membrane and line rinsed with dichloromethane (16.1 Kg). The phases were separated and the aqueous phase extracted with dichloromethane (48.2 Kg). The combined organic extracts were washed with 5% w/w sodium hydrogen carbonate solution (48 L). The sodium hydrogen carbonate phase was back extracted with dichloromethane (15.4 Kg). The combined organic extracts were washed with 20% w/w sodium thiosulphate solution (48 L). The sodium thiosulphate phase was back extracted with dichloromethane (16.3 Kg). The combined organic extracts were washed with water (47 L). The water phase was back extracted with dichloromethane (16.4 Kg). The combined organic extracts were recharged to the vessel, line rinsed with dichloromethane (31.3 Kg) and concentrated to ca. 48 L at atmospheric pressure. Dichloromethane (63 Kg) was charged and the batch concentrated to ca. 48 L at atmospheric pressure.

Dichloromethane (66 Kg) was charged and the batch concentrated to ca. 48 L at atmospheric pressure. Dichloromethane (63.6 Kg) was charged and the batch concentrated to ca. 48 L at atmospheric pressure. Dichloromethane (63.8 Kg) was charged and the batch concentrated to ca. 48 L at atmospheric pressure. Dichloromethane (77.8 Kg) was charged and the batch concentrated to ca. 48 L at atmospheric pressure. Acetonitrile (47.7 Kg) was charged and the batch concentrated to ca. 96 L at atmospheric pressure. Acetonitrile (46.4 Kg) was charged and the batch concentrated to ca. 96 L at atmospheric pressure. The batch was cooled to 18° C. to 23° C., stirred for 2.5 hours and then filtered. The filter cake was washed twice with acetonitrile (19.6 Kg) at ca. 20° C. and then dried at up to 55° C. in vacuo to provide the subtitle compound as a pale yellow solid (16.74 Kg).

$^1$H NMR $\delta_{(DMSO)}$ 8.51 (1H, d), 8.01-7.94 (2H, m), 7.72 (1H, d).

c) 2,6-Dichloro-quinoline-5-carboxylic acid 2.09M Isopropyl magnesium chloride (27.0 L) was charged to a vessel containing 2,6-dichloro-5-iodoquinoline (15.0 Kg) and degassed tetrahydrofuran (103.4 Kg) at 18° C. to 25° C. Tetrahydrofuran (13.9 Kg) was charged as a line rinse. The reaction was stirred at 18° C. to 25° C. for 15 minutes, cooled to 10° C. to 15° C. and sparged with gaseous carbon dioxide for ca. 6 hours whilst maintaining the temperature at 5° C. to 25° C. Methanol (12.3 Kg) was charged to the vessel at 15° C. to 20° C., stirred for ca. 30 minutes and then diluted further with water (134.0 Kg). The batch was concentrated to ca. 135 L by vacuum distillation (<40° C.). The concentrate was diluted with water (121 Kg), ethyl acetate (40.7 Kg) and adjusted to 20° C. to 25° C. The phases were split and the aqueous phase washed with ethyl acetate (3×40.8 Kg). The pH of the aqueous phase was adjusted to pH 5.09 using 1M hydrochloric acid (3.97 L) and washed twice with tert-butylmethylether (23.4 Kg). The pH of the aqueous phase was adjusted to pH 1.35 using 2M hydrochloric acid (25.5 L), stirred for ca. 1 hour at 22° C. and filtered. The filter cake was washed 4 times with water (ca. 60 L) at ca. 20° C. and then dried at up to 55° C. in vacuo to provide the subtitle compound as a pale yellow solid (8.74 Kg).

$^1$H NMR $\delta_{(DMSO)}$ 14.41 (1H, br s), 8.32 (1H, d), 8.10 (1H, dd), 7.97 (1H, d), 7.77 (1H, d).

d) O,O'—(S)-(1,1'-dinaphthyl-2,2'-diyl)-N,N'-di-(R,R)-1-phenylethylphosphoramidite (R—(R,R))-(+)-bis(alpha-methylbenzyl)amine (0.35 Kg) was charged to a vessel containing phosphorous trichloride (0.1365 Kg), toluene (3.15 L) and triethylamine (0.714 L) whilst maintaining the temperature at 18° C. to 25° C. Toluene (0.35 L) was charged as a line rinse. After 3.5 hours a solution of (S)-(−)-1,1'-bi(2-naphthol) (0.445 Kg) was charged as a solution in tetrahydrofuran (0.70 L) whilst maintaining the temperature at 20° C. to 26° C. Tetrahydrofuran (0.35 L) was charged as a line rinse. The reaction mixture was stirred for 18 hours at ambient temperature and then filtered through silica [9 cm (h)×19 cm (w)]. The product was eluted with toluene (10×1.75 L). The combined filtrates were concentrated in vacuo to ca. 1 L at <35° C. and then diluted with acetonitrile (5.6 L). The resultant slurry was cooled to 0° C. to 5° C., stirred for ca. 1 hour and then filtered. The filter cake was washed with acetonitrile (2×0.70 L) and dried under nitrogen on the filter to provide the subtitle compound as a colourless solid (0.65 Kg).

$^1$H NMR $\delta_{(CDCl_3)}$ 7.95-7.87 (4H, m), 7.59 (1H, s), 7.47-7.36 (4H, m), 7.29-7.20 (3H, m), 7.18-7.03 (10H, m), 4.58-4.44 (2H, m), 1.72 (6H, d).

e) (S)-3-Methylcyclohexanone

Toluene (38.1 Kg) was charged to a vessel containing O,O'—(S)-(1,1'-dinaphthyl-2,2'-diyl)-N,N'-di-(R,R)-1-phenylethylphosphoramidite (0.448 Kg) and copper(II)trifluoromethanesulphonate (0.132 Kg) and stirred at 21° C. for ca. 90 minutes. The vessel was purged with argon, cooled to −25° C. to −30° C. and charged with cyclohex-2-ene-1-one (14.0 Kg) whilst maintaining the temperature at −25° C. to −30° C. Toluene (12.1 Kg) was charged as a line/vessel rinse. 2M Dimethylzinc in toluene (ca. 84.5 L) was charged maintaining the temperature at −20° C. to −30° C. over ca. 4.5 hours. Toluene (12.5 Kg) was charged as a line/vessel rinse. The reaction was stirred at −20° C. to −30° C. for ca. 10 hours before the batch was quenched onto cooled methanol (54.5 Kg) over ca. 45 minutes whilst maintaining the temperature at <10° C. The batch was diluted with toluene (5.5 Kg), stirred at 7° C. for 1 hour, warmed to 18° C. and then stirred for a further 6 hours. The reaction mixture was filtered using a 100 μm and 1 μm filter membrane and the filter cake was washed twice with toluene (13 Kg) at ca. 20° C. The reaction mixture was concentrated to 70 L at atmospheric pressure and then purified by wiped film distillation to provide the subtitle compound (13.13 Kg) as a solution in toluene.

$^1$H NMR $\delta_{(CDCl_3)}$ 2.45-2.15 (3H, m), 2.10-1.80 (4H, m), 1.75-1.55 (1H, m), 1.40-1.25 (1H, m), 1.05 (3H, d).

f) (3S,5S)-5-Methyl-1-oxa-spiro[2.5]octane

A solution of potassium tert-butoxide (11.6 Kg) in dimethylsulfoxide (36 Kg) was charged to a mixture of trimethylsulfoxonium iodide (22.68 Kg) in dimethylsulfoxide (36.2 Kg) whilst maintaining the temperature at 15° C. to 25° C. Dimethylsulfoxide (11.5 Kg) was charged as a line/vessel rinse and the batch stirred at 15° C. to 25° C. for 90 minutes. A toluene solution (61.02 Kg) containing 3-methyl-cyclohexanone (10.50 Kg) was charged to the reaction whilst maintaining the temperature at 15° C. to 25° C. Toluene (9.9 Kg) was charged as a line/vessel rinse. The batch was stirred for 2 hours, quenched by the addition of water (94.5 Kg) whilst maintaining the temperature at 15° C. to 25° C. and then filtered. Water (11.0 Kg) was charged as a line/vessel rinse. The phases were split and the organic phase retained as a solution of the subtitle compound (11.1 Kg) in toluene.

$^1$H NMR $\delta_{(CDCl_3)}$ 2.61 (2H, dd), 2.00-1.36 (6H, m), 1.32-1.16 (2H, m), 1.05-0.80 (4H, m).

g) (1S,3S)-1-[(Benzylamino)methyl]-3-methyl-cyclohexanol. HCl

Benzylamine (20.4 Kg) was charged to a toluene solution (72.3 Kg) of (3S,5S)-5-Methyl-1-oxa-spiro[2.5]octane (9.69 Kg) and isopropanol (22.2 Kg) whilst maintaining the temperature at 15° C. to 25° C. Isopropanol (15.6 Kg) was charged as a line/vessel rinse and the batch adjusted to 68° C. to 72° C. After ca. 5.5 hours the batch was cooled to 6° C. and charged with hydrochloric acid in isopropanol [prepared with acetyl chloride (24.4 Kg) and isopropanol (26.7 Kg)] such that the temperature was maintained at 0° C. to 20° C. Cooled tert-butylmethyl-ether (35.9 Kg) was charged whilst maintaining the temperature at 0° C. to 20° C. and then stirred at ca. 10° C. for 90 minutes. The resultant slurry was filtered, the filter cake washed twice with tert-butylmethylether (ca. 35 Kg) at ca. 10° C. and then dried on the filter under vacuum for ca. 10 hours to provide the subtitle compound as a colourless solid (20.29 Kg).

$^1$H NMR $\delta_{(CDCl_3)}$ 9.40 (1H, br s), 7.63-7.60 (2H, m), 7.44-7.36 (3H, m), 4.31 (1H, s), 4.23 (2H, s), 2.74 (2H, s), 2.10-1.45 (7H, m), 1.11 (1H, dt), 0.83 (3H, d), 0.87-0.68 (1H, m).

h) (1S,3S)-1-Aminomethyl-3-methyl-cyclohexanol. HCl

20% w/v sodium hydroxide (50 L) was charged to a vessel containing (1S,3S)-1-[(benzylamino)methyl]-3-methylcyclohexanol. HCl (25 Kg, 13.93 Kg contained) and tert-butylmethylether (88.6 Kg) whilst maintaining the temperature at 18° C. to 25° C. The phases were split and the aqueous phase extracted twice with tert-butylmethylether (37.2 Kg). The combined organic extracts were recharged to the vessel, line rinsed with tert-butylmethylether (20.2 Kg) and concentrated to ca. 75 L at atmospheric pressure. tert-Butyl methyl ether (52.6 Kg) was charged and the batch concentrated to ca. 75 L at atmospheric pressure. Absolute ethanol (118.6 Kg) was charged and the batch concentrated to ca. 75 L at 30° C. to 45° C. The temperature was adjusted to ca. 20° C. and then charged to a nitrogen-purged vessel containing 5% palladium on carbon (5.00 kg). Absolute ethanol (63.0 Kg) was charged as a vessel/line rinse. The vessel was placed under an atmosphere of hydrogen, adjusted to 58° C. to 62° C. and stirred for 12 hours. The reaction was cooled to 18° C. to 25° C., purged with nitrogen and filtered. Absolute ethanol (20.8 Kg) was recirculated through/around the vessel/lines and filter cake to recover product. Absolute ethanol (19.7 Kg) was recirculated through/around the vessel/lines and filter cake to recover product. The combined filtrates were concentrated to ca. 75 L at 30° C. to 45° C. and then diluted with diisopropylether (132.3 Kg). The reaction mixture was heated to reflux and concentrated to ca. 75 L at atmospheric pressure. Diisopropylether (124.6 Kg) was charged and the batch concentrated to ca. 75 L at atmospheric pressure. Diisopropylether (123 Kg) was charged and the batch concentrated to ca. 75 L at atmospheric pressure. The mixture was cooled to 5° C. to 10° C. and charged with HCl in ethanol [prepared with acetyl chloride (7.68 Kg) and ethanol (49.9 Kg)] such that the temperature was maintained at 5° C. to 20° C. Cooled diisopropylether (73.2 Kg) was charged whilst maintaining the temperature at 5° C. to 20° C. and then stirred at ca. 7° C. for 1 hour. The resultant slurry was filtered, the filter cake washed twice with diisopropylether (ca. 38 Kg) at ca. 20° C. and then dried on the filter under vacuum for ca. 10 hours to provide the subtitle compound as a colourless solid (8.02 Kg).

$^1$H NMR $\delta_{(D_2O)}$ 3.06 (2H, s), 1.84-1.60 (7H, m), 1.44-1.30 (1H, m), 1.10 (1H, t), 1.02-0.87 (4H, m).

i) 2,6-Dichloro-N-{[(1S,3S)-1-hydroxy-3-methylcyclohexyl]methyl}-quinoline-5-carboxamide Thionyl chloride (7.2 Kg) was charged to a vessel containing 2,6-dichloro-quinoline-5-carboxylic acid (5.00 Kg) and toluene (43.0 Kg). Toluene (13.1 Kg) was charged as a line rinse. The reaction was adjusted to 82° C. to 84° C. and stirred for ca. 7 hours. The batch was cooled to <40° C. and concentrated to ca. 25 L by vacuum distillation at 30° C. to 40° C. Toluene (43.5 Kg) was charged and the batch concentrated to ca. 25 L at 30° C. to 40° C. Toluene (22.0 Kg) was charged and the temperature adjusted to 20° C. to 25° C. This toluene solution was then charged to a cooled mixture of (1S,3S)-1-(aminomethyl)-3-methylcyclohexanol hydrochloride (3.70 Kg), tetrahydrofuran (43.5 Kg) and triethylamine (6.26 Kg) such that the temperature was maintained at 5° C. to 10° C. Toluene (4.6 Kg) was charged as a line rinse. After 4 hours, the temperature was adjusted to 20° C. to 25° C. and quenched by the addition water (25 Kg) whilst maintaining the temperature at 20° C. to 25° C. The temperature was adjusted to 40° C. to 45° C. for 20 minutes before the phases were separated. The organic phase was washed with water (25 L) at 40° C. to 45° C. and then concentrated to 45 L at 25° C. to 40° C. Toluene (42.7 Kg) was charged and the batch concentrated to ca. 45 L at 25° C. to 40° C. Toluene (43.2 Kg) was charged and the batch concentrated to ca. 45 L at 25° C. to 40° C. The reaction mixture was then heated to reflux to achieve full dissolution, cooled to 20° C. to 25° C. over 2.5 hours and then stirred for 2.5 hours at 20° C. to 25° C. The resultant slurry was filtered and the filter cake washed twice with toluene (ca. 9 Kg) at ca. 20° C. and then dried at up to 55° C. in vacuo to provide the subtitle compound as a colourless solid (5.88 Kg).

$^1$H NMR $\delta_{(DMSO)}$ 8.66 (1H, t), 8.25 (1H, d), 8.04 (1H, d), 7.91 (1H, d), 7.76 (1H, d), 4.24 (1H, s), 3.35-3.25 (expected to be 2H, d, however signal is obscured by water signal), 1.85-1.45 (6H, m), 1.32 (1H, dt), 1.05 (1H, t), 0.92-0.71 (4H, m).

j) 6-Chloro-N-{[(1S,3S)-1-hydroxy-3-methylcyclohexyl]methyl}-2-[(3R)-3-hydroxypyrrolidin-1-yl]quinoline-5-carboxamide Methanol (36.9 Kg) was charged to a vessel containing 2,6-dichloro-N-{[(1S,3S)-1-hydroxy-3-methylcyclohexyl]methyl}-quinoline-5-carboxamide (5.85 Kg), (R)-3-hydroxypyrrolidine hydrochloride (4.15 Kg), acetonitrile (32.5 Kg) and triethylamine (9.8 Kg). The vessel was heated to reflux. After ca. 70 hours the batch was cooled to 40 to 45° C. and clarified through a 1 µm filter membrane. Methanol (4.7 L) was charged as a vessel/line rinse and the batch concentrated to ca. 29 L at atmospheric pressure.

Acetonitrile (46.8 Kg) was charged and the batch concentrated to ca. 29 L at atmospheric pressure. Acetonitrile (46.8 Kg) was charged and the batch concentrated to ca. 29 L at atmospheric pressure. The batch was cooled to 18° C. to 25° C., diluted with water (56.5 Kg) and stirred for 1 hour. The resultant slurry was filtered, the filter cake washed twice with water (ca. 30 Kg) and then dried at up to 45° C. in vacuo to provide the title compound as a colourless solid [5.6 Kg, 100% ee, 98.5% de (excess over all possible stereoisomers as determined by analytical stereochemical HPLC)].

$^1$H NMR $\delta_{(DMSO)}$ 8.53 (1H, t), 7.84 (1H, d), 7.59-7.51 (2H, 2×d), 6.99 (1H, d), 5.03 (1H, d), 4.45 (1H, br s), 4.19 (1H, s), 3.79-3.41 (4H, m), 3.31 (2H, d), 2.13-1.29 (9H, m), 1.08 (1H, t), 0.94-0.73 (4H, m).

Pharmacological Analysis

P2X$_7$ Assay

Certain compounds such as benzoylbenzoyl adenosine triphosphate (bbATP) are known to be agonists of the P2X$_7$ receptor, effecting the formation of pores in the plasma membrane (Drug Development Research (1996), 37(3), p. 126). Consequently, when the receptor is activated using bbATP in the presence of ethidium bromide (a fluorescent DNA probe), an increase in the fluorescence of intracellular DNA-bound ethidium bromide is observed. The increase in fluorescence can be used as a measure of P2X$_7$ receptor activation and therefore to quantify the effect of a compound on the P2X$_7$ receptor.

In this manner, each of the title compounds of the Examples was tested for antagonist activity at the P2X$_7$ receptor. Thus, the test was performed in 96-well flat bottomed microtitre plates, the wells being filled with 250 µl of test solution comprising 200 µl of a suspension of THP-1 cells (2.5×10$^6$ cells/ml) containing 10$^{-4}$M ethidium bromide, 25 µl of a high potassium buffer solution containing 10$^{-5}$M bbATP, and 25 µl of the high potassium buffer solution containing concentrations of test compound typically from 30 µM-0.001 µM. The plate was covered with a plastics sheet and incubated at 37° C. for one hour. The plate was then read in a Perkin-Elmer fluorescent plate reader, excitation 520 nm, emission 595 nm, slit widths: Ex 15 nm, Em 20 nm. For the purposes of comparison, bbATP (a $P2X_7$ receptor agonist) and pyridoxal 5-phosphate (a $P2X_7$ receptor antagonist) were used separately in the test as controls. From the readings obtained, a $pIC_{50}$ figure was calculated for each test compound, this figure being the negative logarithm of the concentration of test compound necessary to reduce the bbATP agonist activity by 50%.

hERG Binding Protocol

The hERG assay was performed according to the procedure described in WO2005/037052. The affinity ($pIC_{50}$) of compounds for the ion channel subunit encoded by the human ether-a-go-go-related gene (hERG) gene was determined by competition binding of radioligand 3,7-Bis[2-(4-nitro[3,5-$^3$H]phenyl)ethyl]-3,7-diazabicyclo[3.3.1]nonane to HEK (human embryonic kidney) cell membranes expressing hERG, in a filter wash format.

Membranes were incubated for 3 hours at room temperature with serial dilutions of the test compounds, radioligand 3,7-Bis[2-(4-nitro[3,5-$^3$H]phenyl)ethyl]-3,7-diazabicyclo[3.3.1]nonane at 1 nM final concentration, and assay buffer (10 mM HEPES, 130 mM NaCl, 5 mM KCl, 1 mM EGTA, 0.8 mM $MgCl_2$, pH 7.4). The assay was conducted in a final volume of 200 µL, in the presence of 1% (v/v) dimethyl sulphoxide. Non-specific binding was determined by measuring the binding of 3,7-Bis[2-(4-nitro[3,5-$^3$H]phenyl)ethyl]-3,7-diazabicyclo[3.3.1]nonane in the presence of 10 µastemizole. During this incubation GF/B filter plates were immersed in coating solution 0.3% (v/v) Polyethylenimine and 0.2% (w/v) BSA). Following incubation assay plates were harvested onto precoated GF/B filter plates using a Tomtec harvester.

The $pIC_{50}$, defined as the negative logarithm of the concentration of compound required for 50% reduction in 3,7-Bis[2-(4-nitro[3,5-$^3$H]phenyl)ethyl]-3,7-diazabicyclo[3.3.1]nonane binding, was determined. A 'less than' figure indicates <50% inhibition at the quoted concentration, this being the highest concentration tested.

Results

Each of the compounds of the Examples demonstrated very high $P2X_7$ antagonist activity, having a $pIC_{50}$ figure $\geq 8.0$. Moreover, each of the compounds displayed particularly low hERG activity, with less than 50% inhibition at the highest concentration tested. Table 1 shows $P2X_7$ $pIC_{50}$ values and hERG $pIC_{50}$ values for Examples 1-4 (isomer 2), and comparative compounds exemplified in WO 2004/106305 (Examples 29, 36, 44 and 50).

TABLE 1

| Example Number | $P2X_7$ $pIC_{50}$ | hERG $pIC_{50}$ | $P2X_7$:hERG Ratio |
|---|---|---|---|
| 1 | 8.1 | <4 | >10,000 |
| 2 | 8.1 | <4 | >10,000 |
| 3 | 8.1 | <4 | >10,000 |
| 4 - isomer 2 | 8.0 | <4 | >10,000 |
| 29 WO 2004/106305 | 7.2 | 4.5 | 502 |
| 44 WO 2004/106305 | 7.9 | 4.9 | 1000 |
| 36 WO 2004/106305 | 8.2 | 5.1 | 1258 |
| 50 WO 2004/106305 | 7.5 | 4.9 | 398 |

Compounds according to the present invention registered a $P2X_7$ $IC_{50}$ value at concentrations of 10 nM or lower. Further, they did not display sufficient activity to register an $IC_{50}$ for hERG at a concentration of 100 µM. Accordingly, the compounds of the present invention have a ratio of $P2X_7$:hERG affinity of >10,000. The comparative compounds, Examples 29, 36, 44 and 50 of WO 2004/106305, respectively registered a hERG $IC_{50}$ at a concentration of 32 µM, 8 µM, 13 µM and 13 µM and required a concentration of 63 nM, 6 nM, 13 nM and 32 nM to register a $P2X_7$ $IC_{50}$. Accordingly, their $P2X_7$:hERG affinity ratios are just 502, 1258, 1000 and 398 respectively.

Bioavailability—Rat PK

Pharmacokinetic parameters and concepts are used in DMPK to describe the fate of a compound in the body. The distribution and excretion of a compound are reflected in the plasma concentration-time profile. By appropriate dosing, sampling and analysis key parameters (clearance, volume, half-life, bioavailability etc.) can be determined.

Test compounds were typically dosed intravenously to the right lateral tail vein of male Sprague Dawley rats at a dose level of 3 mg/kg (1 ml/kg) in DMA:water (40:60 v/v). Rats were dosed orally at a dose level of 5 mg/kg (2 ml/kg) in 0.5% hydroxypropylmethylcellulose (HPMC, w/v)/0.1% Tween 80 (v/v) in water). Following IV administration, serial blood samples (200 µl) were taken from the left lateral tail vein at 2, 4, 8, 15, 30, 60, 120, 180, 300, 420, 720 and 1440 min and at 0, 20, 40, 60, 120, 180, 300, 420, 720 and 1440 min following oral administration. Plasma was prepared by centrifugation.

To determine the plasma levels of test compound, 50 µl of methanol was added to 50 µl of each of the test samples, whilst 40 µl of methanol was added to the 50 µl aliquots of control plasma containing 10 µl spikes of authentic standard used to create a calibration line and QCs. Finally, 100 µl of methanol containing a chemically similar internal standard was added to each sample, standard and QC giving a final volume of 200 µl. All plasma samples were then thoroughly mixed and placed at −20° C. for at least an hour prior to centrifugation. The resultant supernatants were analysed by HPLC-MSMS after an appropriate, selective and sensitive method had been created by optimizing both cone voltage and collision energy.

Pharmacokinetic parameters were derived from concentration-time using non-compartmental analysis in WinNonLin®. Bioavailability was calculated using the following equation $F=AUC_{PO}*Dose_{IV}/AUC_{IV}*Dose_{PO}$.

Rat po Bioavailability for Example 2=59%

In Vitro Phospholipidosis Protocol

Assessment of a compounds potential to induce phospholipidosis was determined by an in vitro fluorescent assay which reports the accumulation of phospholipids in primary rat hepatocytes. Hepatocytes were isolated from Han Wistar rats by a 2-stage collagenase digest method. The hepatocytes were then plated on collagen coated 96-well plates in William's E medium. The cells were left to adhere for 1 hour then the media was replaced with a solution of 250 µg·ml$^{-1}$ collagen in Hepatozyme cell culture medium.

Cells were then cultured for 48 hours with the medium being changed at 24 hours. At 48 hours post isolation the medium was changed to Hepatozyme supplemented with the fluorescent phospholipid N-(6-tetramethylrhodaminethio-carbamoyl)-1,2-dihexadecanoyl-sn-glycero-3-phosphoethanolamine (DHPE-TRITC) (5 µg·ml$^{-1}$). At this time, test compounds were added to the hepatocytes at a range of concentrations in a serial dilution with a final concentration of 0.4% dimethylsulfoxide (used as solvent for test compounds).

The cells were incubated for a further 24 hours and then fixed by addition of a phosphate buffered saline (PBS) solution containing the nuclear stain Hoechst 33342 (final concentration 2 µM) and paraformaldehyde solution (final concentration 4%). The plates were kept at room temperature for 30 minutes then washed three times in PBS solution.

Images of the hepatocytes were then acquired using an automated microscope platform (GE In Cell Analyser 3000). Image analysis algorithms were then used to assess cell viability and the accumulation of the DHPE-TRITC label within viable hepatocytes. The quantified accumulation observed with test compounds was then normalised to a range of 0, representing the accumulation observed in cells exposed to vehicle only, and 1, representing cells exposed to 10 µM amiodarone. The maximum accumulation across the dose response of the test compound, where cell viability is >50%, is reported, as is the dose at which this maximum was observed. The lowest dose that caused >50% cell toxicity is also reported. Toxicity in individual cells is identified as a change in nuclear labelling to a condensed, punctate morphology.

The dose at which phospholipidosis is observed is known to be inversely correlated with the in vivo incidence of phospholipidosis (David K Monteith, Ryan E Morgan & Bartley Halstead (2006) "In vitro assays and biomarkers for drug-induced phospholipidosis". Expert Opinion on Drug Metabolism & Toxicology, vol. 2 (5), pp 687-696).

Example 2 according to the present invention registered no measurable accumulation even at a maximum test concentration of 250 uM. Further it registered a minimum toxic concentration of >250 uM.

Measurement of Plasma Protein Binding

The extent of plasma protein binding was determined via equilibrium dialysis of a compound between human plasma and aqueous buffer at 37° C., and determination of the concentrations of compound in the plasma and buffer by HPLC-MS/MS.

Dialysis cells (molecular weight cut-off 5000) were prepared by rinsing with water followed by soaking in the dialysis buffer for a minimum of 1 hour. The dialysis buffer was isotonic buffered saline pH 7.4. Stock solutions of compound in dimethylsulfoxide were prepared at a concentration of 0.5 mM.

The stock DMSO solution of compound was added to the plasma at a ratio of 10 µl of DMSO to each ml of plasma. This gave a 1% DMSO in plasma solution with each compound at a concentration of 5 µM.

Dialysis cells were then prepared and one half of the cell filled with 750 µl of dialysis buffer and the other half of the cell with 750 µl of plasma solution of compound. Once prepared the cells were sealed and placed in an incubator box at 37° C. These cells were then rotated for a minimum of 4 hours to equilibrate.

After equilibration 500 µl of the buffer samples were removed and added to HPLC vials along with 100 µl of plasma (sample in 6-fold diluted plasma), and 100 µl of the plasma samples were removed and added to HPLC vials along with 500 µl of dialysis buffer (sample in 6-fold diluted plasma).

The samples were then analysed using HPLC-MS/MS. A four point calibration curve was obtained by dilutions of the stock solutions with 6-fold diluted plasma at concentrations of 0.013 µM, 0.05 µM, 0.25 µM and 1.25 µM which were injected in this order followed by the buffer sample and then the plasma sample.

Calculation

The concentration of compound in the samples were determined using MassLynx version 4.1 software (produced by Waters/Micromass) that automatically calculated a calibration curve and interpolated the concentration of compound in the analytes. Plasma protein binding was determined from the measured concentration as the percentage of compound bound in plasma (% bound) using the following equation;

$$\% \text{ bound} = 100 - 100\left(\frac{1.05(6*\text{plasma } conc - 1.2*\text{buffer } conc)}{1.05(6*\text{plasma } conc - 1.2*\text{buffer} \cdot conc) + 1.2*\text{buffer } conc}\right)$$

Human Plasma Protein Binding(% bound) of Example 2 = 88%.

The invention claimed is:

1. A compound of formula (I) or a pharmaceutically acceptable salt thereof:

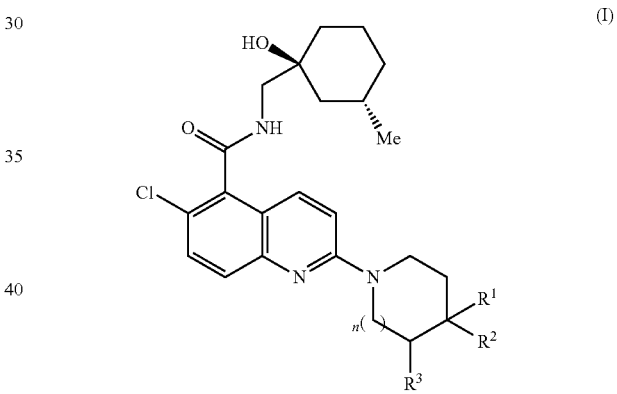

wherein n is 0 or 1;
when n is 0, $R^1$ represents hydrogen or methyl, $R^2$ represents hydroxyl and $R^3$ represents hydrogen; and
when n is 1, $R^1$ represents hydrogen and one of $R^2$ and $R^3$ represents hydroxyl and the other of $R^2$ and $R^3$ represents hydrogen.

2. A compound according to claim 1, or a pharmaceutically acceptable salt thereof, wherein n is 0, $R^1$ represents hydrogen or methyl, $R^2$ represents hydroxyl and $R^3$ represents hydrogen.

3. A compound according to claim 2, or a pharmaceutically acceptable salt thereof, wherein $R^1$ represents hydrogen.

4. A compound according to claim 2, or a pharmaceutically acceptable salt thereof, wherein $R^1$ represents methyl.

5. A compound according to claim 1, or a pharmaceutically acceptable salt thereof, wherein n is 1, $R^1$ represents hydrogen and one of $R^2$ and $R^3$ represents hydroxyl and the other of $R^2$ and $R^3$ represents hydrogen.

6. A compound according to claim 5, or a pharmaceutically acceptable salt thereof, wherein $R^2$ represents hydroxyl and $R^3$ represents hydrogen.

7. A compound according to claim 5, or a pharmaceutically acceptable salt thereof, wherein $R^2$ represents hydrogen and $R^3$ represents hydroxyl.

8. A compound of formula (I), selected from:
   6-chloro-N-{[(1S,3S)-1-hydroxy-3-methylcyclohexyl]methyl}-2-[(3S)-3-hydroxypyrrolidin-1-yl]quinoline-5-carboxamide,
   6-chloro-N-{[(1S,3S)-1-hydroxy-3-methylcyclohexyl]methyl}-2-[(3R)-3-hydroxypyrrolidin-1-yl]quinoline-5-carboxamide,
   6-chloro-N-{[(1S,3S)-1-hydroxy-3-methylcyclohexyl]methyl}-2-(4-hydroxypiperidin-1-yl)quinoline-5-carboxamide, and
   6-chloro-N-{[(1S,3S)-1-hydroxy-3-methylcyclohexyl]methyl}-2-(3-hydroxy-3-methylpyrrolidin-1-yl)quinoline-5-carboxamide
   or a pharmaceutically acceptable salt thereof.

9. A pharmaceutical composition comprising a compound of formula (I), or a pharmaceutically acceptable salt thereof, as claimed in any one of claims 1 to 8 in association with a pharmaceutically acceptable adjuvant, diluent or carrier.

10. A process for the preparation of a pharmaceutical composition which comprises mixing a compound of formula (I), or a pharmaceutically acceptable salt thereof, as defined in any one of claims 1 to 8 with a pharmaceutically acceptable adjuvant, diluent or carrier.

11. A method of treating rheumatoid arthritis comprising administering a therapeutically effective amount of a compound of formula (I), or a pharmaceutically acceptable salt thereof, as claimed in any one of claims 1 to 8 to a patient in need thereof.

12. A process of preparing a compound of formula (I) as defined in any one of claims 1 to 8, which comprises:
   (a) reacting a compound of formula (II)

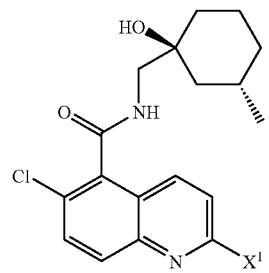

wherein $X^1$ represents a suitable leaving group with a compound of formula (III)

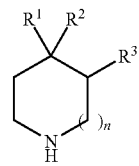

wherein $R^1$, $R^2$, $R^3$ and n are as defined in formula (I), and optionally forming a pharmaceutically acceptable salt of the compound.

13. A compound which is (1S,3S)-1-(aminomethyl)-3-methylcyclohexanol, or a salt thereof.

14. The compound or salt as claimed in claim 13, wherein the compound or salt is optically pure.

15. The compound or salt as claimed in claim 13 or 14, wherein the compound or salt is in substantially pure form.

* * * * *

UNITED STATES PATENT AND TRADEMARK OFFICE
CERTIFICATE OF CORRECTION

PATENT NO. : 7,964,616 B2  Page 1 of 1
APPLICATION NO. : 12/052908
DATED : June 21, 2011
INVENTOR(S) : Ebden et al.

It is certified that error appears in the above-identified patent and that said Letters Patent is hereby corrected as shown below:

On the Title of the patent, right hand column (Other Publications), line immediately before "(Continued)," "*Imtnunol.*", should read -- *Immunol.* --.

Signed and Sealed this

Thirteenth Day of September, 2011

David J. Kappos
*Director of the United States Patent and Trademark Office*